United States Patent
Chung et al.

(10) Patent No.: US 9,550,078 B2
(45) Date of Patent: Jan. 24, 2017

(54) EDAR LIGAND DERIVED PEPTIDES AND USE THEREOF

(75) Inventors: Yong Ji Chung, Yongin-si (KR); Eun Mi Kim, Gunpo-si (KR)

(73) Assignee: CAREGEN CO., LTD., Gunpo-si (KR)

( * ) Notice: Subject to any disclaimer, the term of this patent is extended or adjusted under 35 U.S.C. 154(b) by 114 days.

(21) Appl. No.: 14/236,406

(22) PCT Filed: May 9, 2012

(86) PCT No.: PCT/KR2012/003641
§ 371 (c)(1),
(2), (4) Date: Jun. 2, 2014

(87) PCT Pub. No.: WO2013/018977
PCT Pub. Date: Feb. 7, 2013

(65) Prior Publication Data
US 2014/0255338 A1    Sep. 11, 2014

(30) Foreign Application Priority Data
Aug. 4, 2011 (KR) .......................... 10-2011-0077569

(51) Int. Cl.
*C07K 14/525* (2006.01)
*A61Q 7/00* (2006.01)
*A61K 8/64* (2006.01)
*A61Q 19/08* (2006.01)
*A61Q 19/00* (2006.01)
*A61K 38/00* (2006.01)

(52) U.S. Cl.
CPC . *A61Q 7/00* (2013.01); *A61K 8/64* (2013.01); *A61Q 19/00* (2013.01); *A61Q 19/007* (2013.01); *A61Q 19/08* (2013.01); *C07K 14/525* (2013.01); *A61K 38/00* (2013.01)

(58) Field of Classification Search
None
See application file for complete search history.

(56) References Cited

U.S. PATENT DOCUMENTS

| 2003/0023991 A1* | 1/2003 | Zonana ................. C07K 14/47 800/8 |
| 2010/0260673 A1 | 10/2010 | Cao et al. |
| 2011/0044989 A1 | 2/2011 | Samoylova et al. |

OTHER PUBLICATIONS

International Search Report for International Application No. PCT/KR2012/003641, mailed Nov. 14, 2012 (6 pages).

* cited by examiner

*Primary Examiner* — David Romeo
(74) *Attorney, Agent, or Firm* — Clark & Elbing LLP; Susan M. Michaud (57) ABSTRACT

The present invention relates to novel peptides derived from an EDAR (EDAR receptor) ligand which belongs to TNF (tumor necrosis factor)-α family and to uses of the same. The present peptides of EDA3 derived from EDA and EDphD1 derived from EDAR ligand possess identical or similar activities to naturally occurring EDA and have much higher stability and skin penetration potency than naturally occurring EDA. Therefore, the composition containing the present peptide not only shows excellent effects on improvement in hair loss and promotion of hair growth, but also has superior efficacies on treatment of an EDA signal transduction pathway-related disorder. In addition, the outstanding activity and stability of the present peptide described above may be greatly advantageous in application to pharmaceutical compositions, quasi-drugs and cosmetics.

7 Claims, 8 Drawing Sheets

Fig. 1

Sequence 1 Peptide          Sequence 2 Peptide

Sequence 1

Fig. 3b

Sequence 2

Fig. 4a

Sequence 1

Fig. 4b

Sequence 2

Fig. 5a

Sequence 1

Fig. 5b

Sequence 2

Fig. 6a

Sequence 1

Fig. 6b

Sequence 2

Fig. 7

EDAR LIGAND DERIVED PEPTIDES AND USE THEREOF

CROSS-REFERENCE TO RELATED APPLICATIONS

This application is the U.S. national stage filing under 35 U.S.C. §371 of PCT International Application PCT/KR2012/003641, filed May 9, 2012, which claims priority from KR Patent Application 10-2011-0077569, filed Aug. 4, 2011.

BACKGROUND OF THE INVENTION

Field of the Invention

The present invention relates to an EDAR (EDA receptor)-derived novel peptide and use thereof.

Description of the Related Art

Hair follicle is a peculiar skin organ of mammals, which is developed from the bottom of primitive epidermis into much internal skin layer. The plug of cells known as follicle or dermal papilla exists in the base of the hair follicle (Stenn and Paus, *Physiol. Rev.*, 81: 449 (2002)), and papilla is essential in normal circulation of the hair follicle (Oliver, *Embryol. Exp. Morph.* 15: 331 (1966); Oliver, *Embryol. Exp. Morph.* 16: 231 (1967)) and in growth of the hair shaft. The hair shaft is a thread-shaped epithelial cells that are composed of keratin filaments and filament-aggregating proteins tightly attached thereto.

Human hair follows a growth cycle with three distinct phases: anagen, catagen, and telogen phases. The hair growth cycle is regulated by hormones or many growth factors. Severe stress or malnutrition may advance the catagen and telogen phases, leading to severe hair loss (alopecia) (Arck, *American Journal of Pathology*, 162 (3): 709-712 (2003)). In male pattern baldness, the hair follicles at the front and top of the scalp are sensitive to androgen, which causes the follicles to miniaturize, thereby resulting in hair loss. Briefly, excessive secretion of androgen activates 5-α reductase which causes testosterone to be converted to dihydrotestosterone (DHT). Subsequently, DHT reduces the number of thick dark terminal hairs by shortening a period of hair growth and by miniaturing hair follicles, leading to hair loss. It has been supposed that about 20% of hair loss women suffer from a few disorders called as "female pattern baldness" which the hair often becomes thinner at the top of the scalp. In addition, hair loss broadens with aging. For example, severe hair loss may be caused from different disorders such as cicatricial alopecia or scar conditions including burns or compression injury. Whatever is the cause, while woman power in the workforce has been enhanced and men have cared about their appearance, hair loss may have remarkable psychological, social and sexual impacts as well as loss of pride and self-respect. Although various medicaments have been used to treat hair loss, they are too expensive or give very different adverse effects among individuals. Additionally, it is necessary to take these drugs in a constant manner. In this connection, it is one of serious drawbacks that hair loss may be caused by stopping them. Meanwhile, another demerit is that their efficacies and side effects may be quitely different between individuals.

Therefore, the development of cheaper and more effective novel active ingredient is needed in this industrial field.

Raw materials utilized in cosmetic products have the advantage of being inexpensive, whereas do not give good results since they are composed of plant extract-derived components. It has been known up to now that two commercial drugs (minoxidil and finasteride) may delay only additional hair loss. However, no actual medicaments may have been useful to induce regeneration of new hair follicle in practice. Many scalp cosmetics for preventing hair loss have been commercially available in the market, for example including: (a) a product including a plant extract derived from sophora, hot pepper, Swertia herb, Morus alba, mulberry leaf, ginseng, licorice, peony, foxglove, fennel, Japanese cornel, garlic, and so forth; (b) a composition containing xanthines and growth hormones for not only improving cellular metabolism suppressed by excess dihydrotestosterone (DHT) but also facilitating hair growth through hair loss inhibition and hair regeneration induced by growth hormones; (c) a product containing minerals, vitamins and extracts of green tea, rosemary, mugwort or licorice, which supplies nutrients to the scalp and hair for preventing hair loss and promoting hair growth; and (d) a male pattern baldness product mixing the substances such as vitamin B, vitamin C, vitamin D, vitamin E, nicotinic acid, pantothenic acid, biotin, folic acid, etc. with plant extracts, which inhibits 5-α reductases to suppress production of DHT during androgen metabolism and to help hair metabolism by have been developed. However, they have hardly influence on the production of new hair. As another example, a research group of the Jikei University School of Medicine in Tokyo, Japan has developed the product using corosolic acid known to be effective in diabetes, which inhibits 5-α reductases and exhibits an excellent effect on hair growth.

Many factors are associated with each other in the growth and degeneration of hair. For hair production, the present researchers have studied utilizing the effectiveness for: (a) promoting proliferation of fibroblast which is most important for hair root production; and (b) promoting the expression of factors which is important for inducing hair follicle formation and differentiation of hair.

EDA (Ectodysplasin), which belongs to the tumor necrosis factor (TNF) family, is known to involve in the development of various ectodermal organs such as hair, tooth, and sweat glands. Defect of EDA is a cause of X-linked hypohidrotic ectodermal dysplasia. Among the isoforms of EDAs, EDA1 is the most important for ectodermal development and exerts its function by binding the specific receptor of EDAR. After EDA1's binding to EDAR, EDARADD (EDAR-associated death domain) and NEMO (NF-κB, Essential Modulator) are activated, and NF-κB translocates into nucleus with the degradation of IκB, the inhibitor of NF-κB. The translocated NF-κB enhances in nucleus the expression of genes capable of promoting the formation of hair follicles such as CTGF/CCN2 and Shh (Sonic hedgehog homolog).

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

For developing peptides having actions identical to naturally occurring EDA1 as well as having more enhanced activity, stability and skin penetration than naturally occurring EDA1 protein, the present inventors have made intensive researches. As a result, the present inventors have prepared two kinds of EDA1 related peptides having excellent characteristics described above on the basis of the amino acid sequence of naturally occurring EDA1 protein, eventually accomplishing the present invention.

Accordingly, it is one object of this invention to provide a peptide essentially consisting of an amino acid sequence selected from the group consisting of amino acid sequences of SEQ ID NO:1 and SEQ ID NO:2.

It is another object of this invention to provide a composition for promoting hair growth or improving hair production containing the aforementioned peptide of this invention as an active ingredient.

It is still another object of this invention to provide a composition for improving skin conditions containing the aforementioned peptide of this invention as an active ingredient.

It is further still another object of this invention to provide a composition for improving or treating an EDA1 (ectodysplasin A1) signal transduction pathway-related disorder containing the aforementioned peptide of this invention as an active ingredient.

Other objects and advantages of the present invention will become apparent from the following detailed description together with the appended claims and drawings.

In one aspect of this invention, there is provided a peptide essentially consisting of an amino acid sequence selected from the group consisting of amino add sequences of SEQ ID NO:1 and SEQ ID NO:2.

For developing peptides having actions identical to naturally occurring EDA1 as well as having more enhanced activity, stability and skin penetration than naturally occurring EDA1 protein, the present inventors have made intensive researches. As a result, the present inventors have prepared two kinds of EDA1 related peptides having excellent characteristics described above on the basis of the amino acid sequence of natural-occurring EDA1 protein and the amino acid sequence of ligand binding to the receptor of EDA1 protein, eventually accomplishing the present invention.

The peptide of the present invention essentially consisting of amino acid sequence which is selected from the group consisting of amino acid sequences of SEQ ID NO:1 and SEQ ID NO:2. The term used herein "peptide" refers to a linear molecule formed by linking between amino acid residues through peptide bonds.

The peptides of the present invention may be prepared by conventional chemical synthesis processes known to one of skill in the art, in particular, solid-phase synthesis techniques (Merrifield, *J. Amer. Chem. Soc.* 85: 2149-54 (1963); Stewart, et al., *Solid Phase Peptide Synthesis,* 2nd. ed., Pierce Chem. Co.: Rockford, 111 (1984)).

The peptide of EDA 3 of the present invention may be prepared by primarily predicting a portion of capable of binding to a receptor protein through random partial synthesis of several portions in EDA1 protein and then optimizing an amino add sequence of the predicted portion. Afterwards, the candidate peptides having the most excellent activity are screened to isolate the peptide of SEQ ID NO:1 of this invention.

The other peptide of EDphD1 of the present invention may be prepared by primarily investigating amino acid sequences capable of specifically binding to the receptor of EDA1 protein (EDAR) through phage display technique and then selecting an optimal amino acid sequence as the candidate peptide. Afterwards, the candidate peptides having the most excellent activity are screened to isolate the peptide of SEQ ID NO:2 of this invention.

The peptides of SEQ ID NO:1 and SEQ ID NO:2 not only have actions similar to naturally occurring EDA1 protein but also shows growth factor activities via binding to a receptor.

The peptides of this invention per se have higher stability than naturally occurring EDA1 protein, and its modification enables to have much higher stability.

Preferably, the peptides of this invention have at their N-terminal a protection group selected from the group consisting of acetyl group, fluorenyl methoxy carbonyl group, formyl group, palmitoyl group, myristyl group, stearyl group and polyethylene glycol (PEG).

The modifications of peptides described above greatly increase the stability of the peptides of this invention. The term used herein "stability" refers to in vivo stability and storage stability (e.g., storage stability at room temperature) as well. The protection group described above protects the peptides from the attack of protease in vivo.

In another aspect of this invention, there is provided a composition for promoting hair growth or improving hair production, containing the aforementioned peptide of this invention as an active ingredient.

In still another aspect of this invention, there is provided a method for promoting hair growth or improving hair production comprising administering to a subject the peptide of this invention.

In further still another aspect of this invention, there is provided a use of the peptide of this invention for manufacturing a medicament to promote hair growth and improve hair production.

Since the present composition comprises EDA1-related peptide of this invention as active ingredients described above, the common descriptions between them are omitted in order to avoid undue redundancy leading to the complexity of this specification.

As demonstrated in Examples below, the EDA1 related peptides of the present derived from human EDA protein have stimulatory activity to cell proliferation in fibroblasts. In addition, by facilitating EDA1-EDAR signaling as a representative signal pathway, the degradation of IκB, which is an inhibitor of NF-κB, through phosphorylation and translocation of NF-κB into the nucleus have been observed after activation of EDARADD and NEMO. Furthermore, the translocated NF-κB enhances expressions of down-stream molecules and proteins having the activity of promoting formation of hair follicles such as Shh (Sonic hedgehog homolog) protein. According to animal experiments based on the above-mentioned results, it could be appreciated that the peptide of the present invention significantly promotes hair growth. Therefore, the composition of the present invention has excellent effects on hair growth and the improvements in skin conditions.

In still another aspect of this invention, there is provided a composition for improving skin conditions containing the peptide of this invention as an active ingredient.

In further still another aspect of this invention, there is provided a method for improving skin conditions comprising administering to a subject the peptide of this invention.

In further still another aspect of this invention, there is provided a use of the peptide of this invention for manufacturing a medicament to improve skin conditions.

According to a preferable embodiment, the improvement in the skin conditions by the present peptide is improvement in wrinkle or skin elasticity, prevention of skin aging, improvement in skin moisture, removal of wound or regeneration of skin.

In still another aspect of this invention, there is provided a composition for preventing or treating an EDA1 (ectodysplasin A1) signal transduction pathway-related disorder containing the peptide of this invention as an active ingredient.

In further still another aspect of this invention, there is provided a method for preventing or treating an EDA1 (ectodysplasin A1) signal transduction pathway-related disorder comprising administering to a subject the peptide of this invention.

In further still another aspect of this invention, there is provided a use of the peptide of this invention for manufacturing a medicament to prevent or treat an EDA1 (ectodysplasin A1) signal transduction pathway-related disorder.

According to a preferable embodiment, the EDA1 (ectodysplasin A1) signal transduction pathway-related disorder includes bone disorder, osteoporosis, or obesity.

According to a preferable embodiment, the composition is a pharmaceutical composition containing: (a) a pharmaceutically effective amount of the peptide having the activity of EDA protein of the present invention; and (b) a pharmaceutically acceptable carrier.

The term used herein "pharmaceutically effective amount" refers to an amount enough to show and accomplish efficacies and activities of EDA1-related peptide of this invention.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered orally or parenterally, and preferably, administered parenterally, e.g., by intravenous, subcutaneous, intramuscular, intraperitoneal, local or transdermal administration.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, the pharmaceutical composition of the present invention may be administered with a daily dosage of 0.001-1000 mg/kg.

According to the conventional techniques known to those skilled in the art, the pharmaceutical composition according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

According to a preferable embodiment, the composition is a cosmetic composition containing: (a) a cosmetically effective amount of the EDA1-related peptide of the present invention; and (b) a cosmetically acceptable carrier.

The term used herein "cosmetically effective amount" refers to an amount enough to accomplish efficacies on improvements in skin conditions described hereinabove.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softner, nutrient liquid, nutrient cream, massage cream, essence, eye cream, cleansing cream, cleansing foam, cleansing water, pack, spray or powder.

Where the cosmetic composition is in the form of paste, cream or gel, it may include animal and vegetable fats, waxes, paraffins, starch, tragacanth, cellulose derivatives, polyethylene glycols, silicones, bentonites, silica, talc, zinc oxide or mixtures of these substances.

In the formulation of powder or spray, it may include lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may include solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may contain liquid diluents, for example water, ethanol or propylene glycol, suspending agents, for example ethoxylated isosteary alcohols, polyoxyethylene sorbitol esters and poly oxyethylene sorbitan esters, micocrystalline cellulose, aluminum metahydroxide, bentonite, agar and tragacanth or mixtures of these substances.

The formulation of cleansing compositions with surfactant may contain aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

Furthermore, the cosmetic compositions of this invention may contain auxiliaries as well as peptides as active ingredients and carriers. The non-limiting examples of auxiliaries include preservatives, antioxidants, stabilizers, solubilizers, vitamins, colorants, odor improvers or mixtures of these substances.

The features and advantages of the present invention will be summarized as follows:

(i) EDA-derived EDA3 peptide and EDAR ligand-derived EDphD1 peptide of the present invention possesses identical or similar activities to naturally occurring EDA;

(ii) the peptides of the present invention have much higher stability and skin penetration potency than naturally occurring EDA;

(iii) therefore, the composition containing the present peptide not only shows excellent effects on improvement in hair loss (for example, promotion of hair growth or production of hair), but also has superior efficacies on treatment of a EDA1 (ectodysplasinA1) signal transduction pathway-related disorder; and (iv) the outstanding activity and stability of the present peptide described above may be greatly advantageous in application to pharmaceutical compositions, quasi-drugs and cosmetics.

The present invention will now be described in further detail by examples. It would be obvious to those skilled in the art that these examples are intended to be more concretely illustrative and the scope of the present invention as set forth in the appended claims is not limited to or by the examples.

EXAMPLES

Preparation Example 1

Synthesis of Asn-Met-Ser-Lys-His-Thr-Thr-Phe-Phe-Gly-Ala (SEQ ID NO:1)

700 mg of chloro trityl chloride resin (CTL resin, Nova Biochem Cat No. 01-64-0021) were introduced into a reactor, to which 10 ml of methylene chloride (MC) were added, followed by agitation for 3 min. After removing solution, 10 ml of dimethylformamide (DMF) were added to the resultant and then agitation was carried out for 3 min, after which the solvent was removed. 10 ml of dichloromethane solution were added to the reactor and 200 mmole of Fmoc-Ala(pbf)-OH (Bachem, Swiss) and 400 mmole of DIEA (N,N'-diisopropyl ethylamine) were then added to the reactor, after which the mixture was dissolved by agitation and reaction was then undertaken with agitating for 1 hr. After washing, methanol and DIEA (2:1) dissolved in DCM (dichloromethane) were reacted with the resin for 10 min, and then the resultant was washed using excess of DCM/DMF (1:1). After removing the solution, 10 ml of DMF were added to the resultant and agitation was performed for 3 min, followed by removing the solvent. 10 ml of a deprotection solution (20% piperidine/DMF) were added to the reactor and agitated for 10 min at room temperature, followed by removing the solution. After adding the same volume of the deprotection solution, the reaction was undertaken for 10 min and solution was removed, followed by washing sequentially with DMF (3 times), MC (1 times) and DMF (1 times) to yield Ala(pbf)-CTL resins. 10 ml of DMF solution was added to a new reactor and then 200 mmole of Fmoc-Gly-OH (Bachem, Swiss), 200 mmole of HoBt and 200 mmole of Bop were added, followed by agitation for solubilization. 400 mmole of DIEA was added to the reactor twice as a fraction and agitation was carried out for at least 5 min to dissolve all solid contents. The dissolved amino acids solution was introduced into the reactor containing the deprotected resin and reaction was undertaken with agitating for 1 hr at room temperature. Following the removal of the reaction solution, the resultant was agitated three times (each for 5 min) with DMF solution to remove unreacted residuals. A small amount of the reacted resin was taken to evaluate extent of reactions by Ninhydrine test. Using the deprotection solution, the deprotection was performed twice in the same manner as described above to yield Gly-Ala(pbf)-CTL resin. After washing with DMF and MC, further Ninhydrine test was carried out and the sequential attachments of amino acids below were performed as described above. Based on the amino acid sequence designed by the present inventors, Fmoc-Phe, Fmoc-Phe, Fmoc-Thr(tBu), Fmoc-Thr(tBu), Fmoc-His(trt), Fmoc-Lys, Fmoc-Ser(tBu) and Fmoc-Asn were sequentially attached to resins. Fmoc-protecting group was removed by thoroughly incubating with the deprotection solution twice for 10 min. For acetylation, acetic anhydride, DIEA and HoBt were incubated with the peptidyl resins for 1 hr. The prepared peptidyl resins were washed three times with DMF, MC and methanol, respectively, and gradually dried under nitrogen atmosphere, after which it was completely vacuum-dried under $P_2O_5$. The dried resins were reacted with 30 ml of a leaving solution [containing 95% trifluroacetic acid (TFA), 2.5% distilled water, 2.5% thioanisole] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was completely dried under nitrogen atmosphere to yield 0.85 g of unpurified peptide 1, Asn-Met-Ser-Lys-His-Thr-Thr-Phe-Phe-Gly-Ala (SEQ ID NO:1) (yield rate; 89.9%). The molecular weight of the final product was determined as 1240.4 (theoretical MW: 1239.5) using a mass analyzer. Peptide 2 (Leu-Leu-Ala-Asp-Thr-Thr-His-His-Arg-Pro-Trp-Thr) (SEQ ID NO:2) was also synthesized by the process described in the above (yield rate; 92.1%). The molecular weight of the final product was determined as 1446.5 (theoretical MW: 1447.5) using a mass analyzer.

TABLE 1

| SEQ ID NO | Amino acid sequence | Analyzed values (mass analyzer) | |
|---|---|---|---|
| | | Analyzed values | Theoretical values |
| 1 | NMSKHTTFFGA | 1240.4 | 1239.5 |
| 2 | LLADTTHHRPWT | 1447.6 | 1446.5 |

Experimental Example 1

Influence of Peptides on Cell Growth

In order to evaluate three peptides prepared in Preparation Example 1 whether they have similar activities of growth factor, SRB (Sulforhodamine B; Sigma-Aldrich) colorimetric assay was carried out using HaCaT kerationcytes (Korean Cell Line Bank) and NIH3T3 fibroblasts (Korean Cell Line Bank) according to Rizzino et al. method (Rizzino, et al. *Cancer Res.*, 48: 4266 (1988)).

HaCaT ketatinocytes and NIH3T3 fibroblasts were cultured in 250 ml-flasks containing EMEM (Eagle's minimal essential media; Gibco, USA) supplemented with 10% FBS (fetal bovine serum; Sigma). Cells cultured were treated with 1% trypsin solution to detach cells from the bottom of culture flasks and centrifuged to collect cell pellets. After cells were resuspended in EMEM not containing FBS, its aliquot ($3 \times 10^3$ cells) was added to each well of 96-well plates and cultured under 5% $CO_2$ for 24 hr at 37° C. After 24-hr culture, the medium was changed with a fresh medium without serum and cells were incubated with empty sample (for normalization) and peptides synthesized aseptically dissolved in 10% distilled water with the respective concentrations of 1 μg/ml, 10 μg/ml and 50 μg/ml for 72 hr under the same conditions as described above. After removing supernatants, cells were fixed with ethanol and then washed three times using PBS (phosphate buffered saline), followed by incubation with SRB solution. Cells were sufficiently washed with 1% acetic acid and observed under a microscope to find living cell condition. In addition, absorbance at 590 nm was measured to analyze cell viability.

Figure 1:
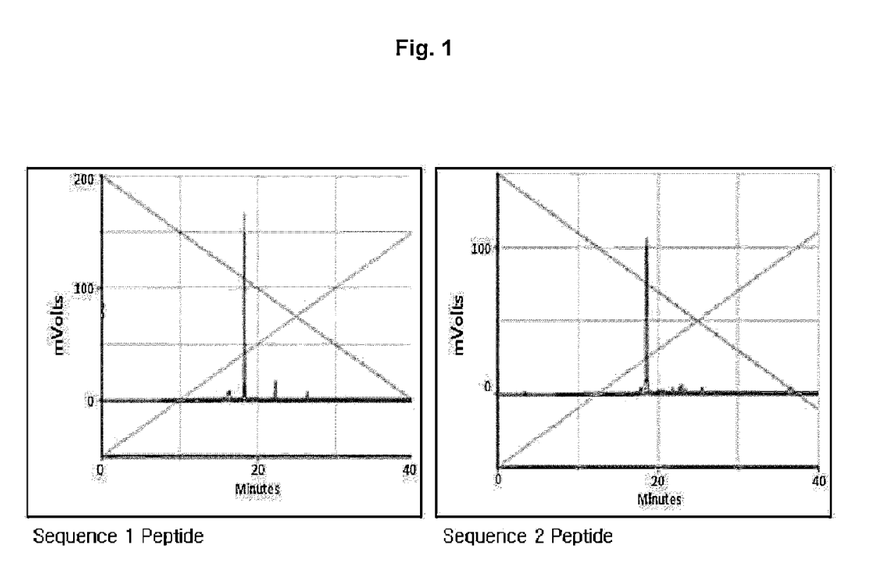
FIG. 1 represents results of HPLC (high performance liquid chromatography) analysis of the peptides of SEQ ID NO:1 and SEQ ID NO:2 prepared in Preparation Example.
Figure 2A:
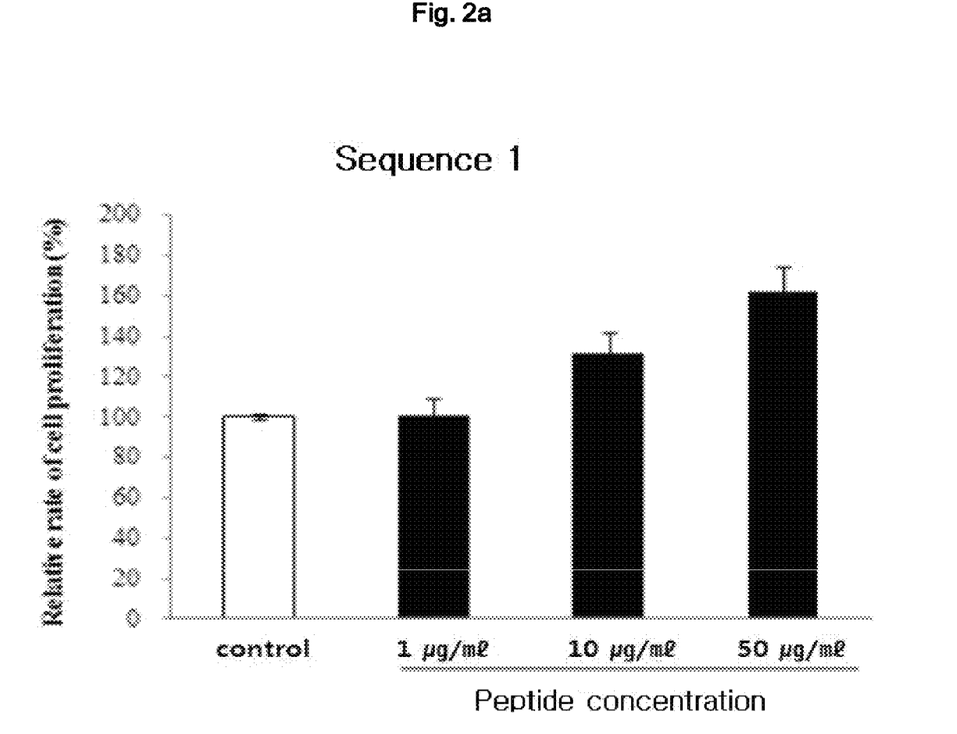
FIG. 2a is a graph representing a stimulatory effect on the growth of fibroblasts treated with the peptide of SEQ ID NO:1 prepared in Preparation Example.
Figure 2B:
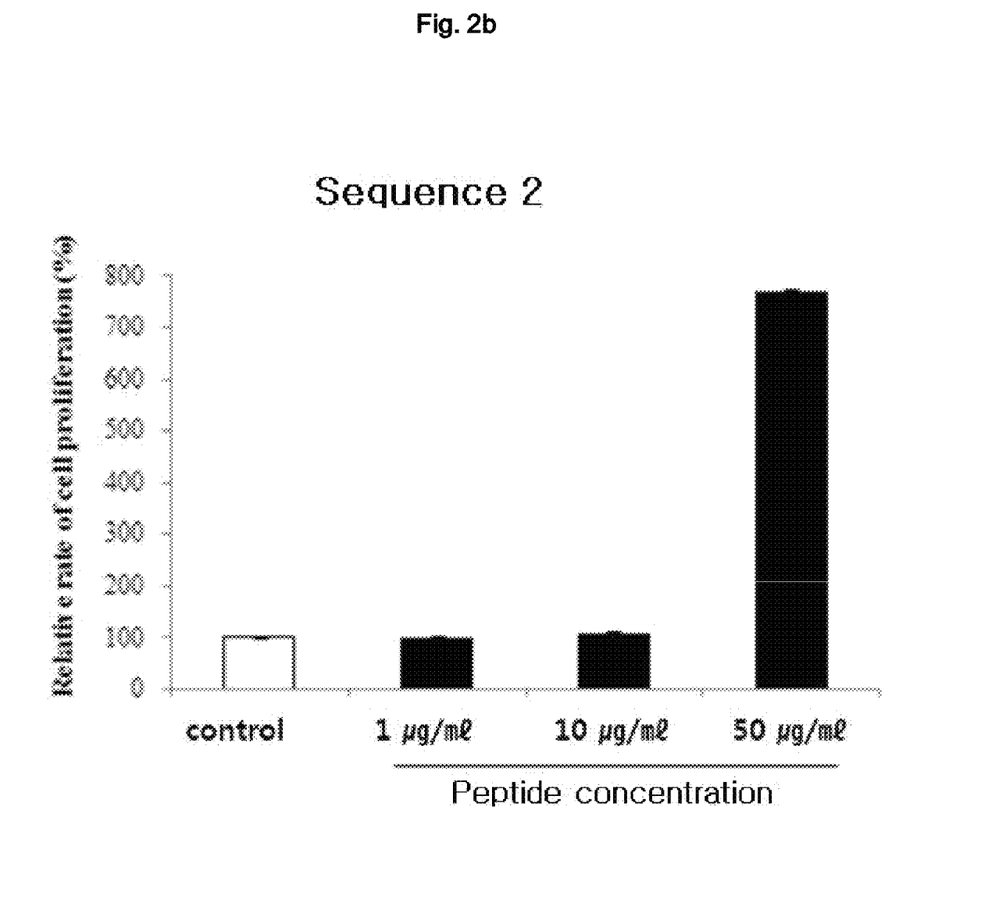
FIG. 2b is a graph representing a stimulatory effect on the growth of fibroblasts treated with the peptide of SEQ ID NO:2 prepared in Preparation Example.

FIGS. 2a and 2b demonstrate that the peptide 1 and 2 of the present invention notably increases the growth of fibroblasts respectively.

Experimental Example 2

Influence of Peptides on Stimulating EDA1-EDAR Signal

Figure 3A:
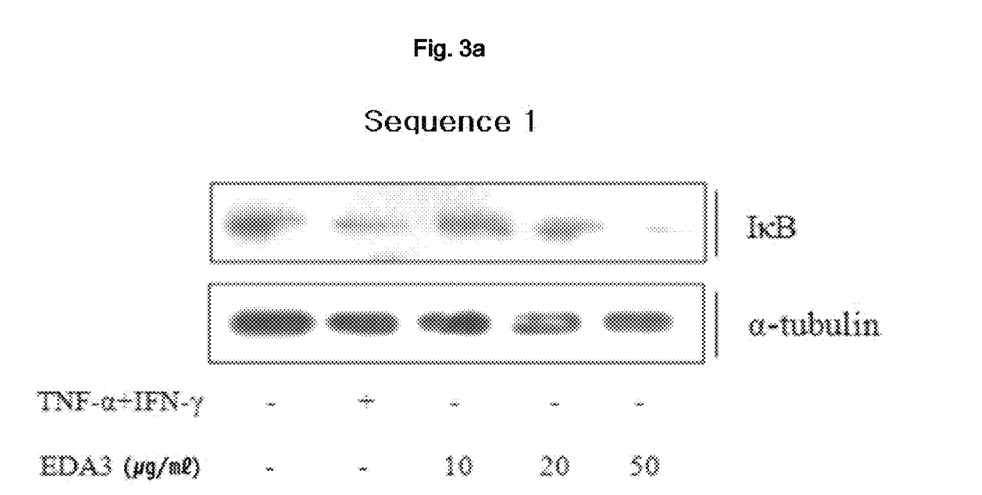
FIG. 3a is a Western blot analysis result showing that cellular amount of IκB protein has been reduced through the phosphorylation followed by ubiquitination when treated with the peptide of SEQ ID NO:1 prepared in Preparation Example.
Figure 3B:
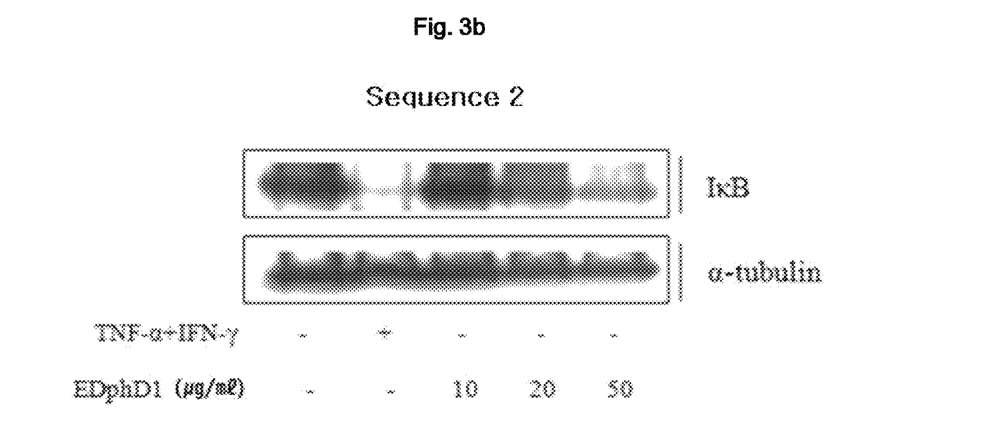
FIG. 3b is a Western blot analysis result showing that cellular amount of IκB protein has been reduced through the ubiquitination following phosphorylation when treated with the peptide of SEQ ID NO:2 prepared in Preparation Example.
Figure 4A:
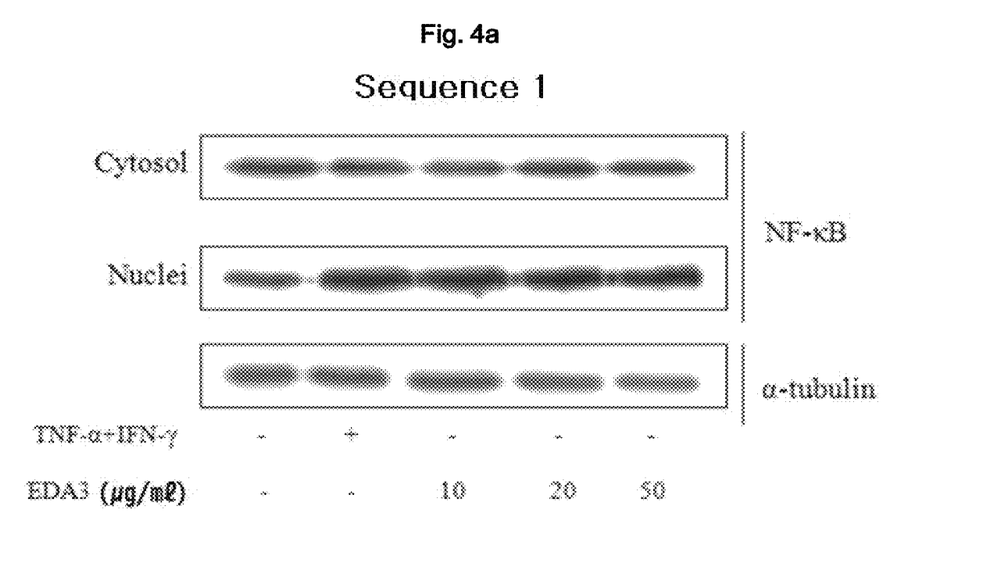
FIG. 4a is a Western blot analysis result showing the translocation of NF-κB into nucleus after activation when treated with the peptide of SEQ ID NO:1 prepared in Preparation Example.
Figure 4B:
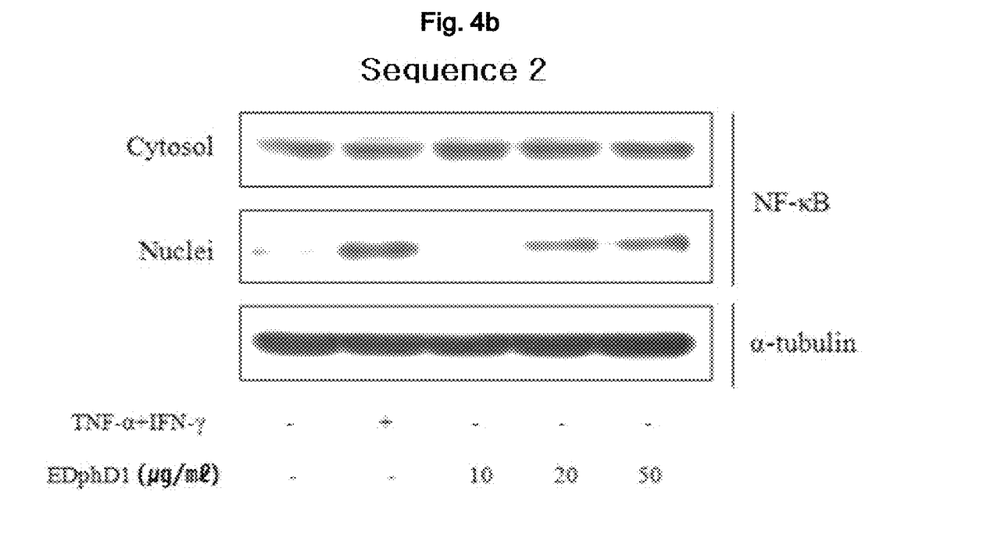
FIG. 4b is a Western blot analysis result showing the translocation of NF-κB into nucleus after activation when treated with the peptide of SEQ ID NO:2 prepared in Preparation Example.

HaCaT kerationcytes were incubated with the peptides synthesized in preparation Example 1 for 20 min. The translocation of NF-κB into nucleus through the phosphorylation of IκB was examined as a representative signaling of EDA protein. The respective effect was measured by Western blot analysis using an antibody against IκB and NF-κB (SantaCruz, USA). The effect of IκB degradation through phosphorylation and uniquitination in a concentration dependent manner of the treated peptides of this invention was confirmed (FIGS. 3a and 3b). Furthermore, the activation and nucleus translocation of NF-κB was also observed after degradation of IκB (FIGS. 4a and 4b). Moreover, in order to prove the effect caused by the translocation of NF-κB into nucleus by the treatment of peptides, the expression levels of IL-1b, IL-6, and COX-2, whose expression are known to be induced by NF-κB, were measured through RT-PCR by using respective specific primers. The expression levels of the above mentioned proteins of IL-1b, IL-6, and COX-2 were increased with the translocations of NF-κB into nucleus which is induced by the treatments of the peptides.

Figure 5A:
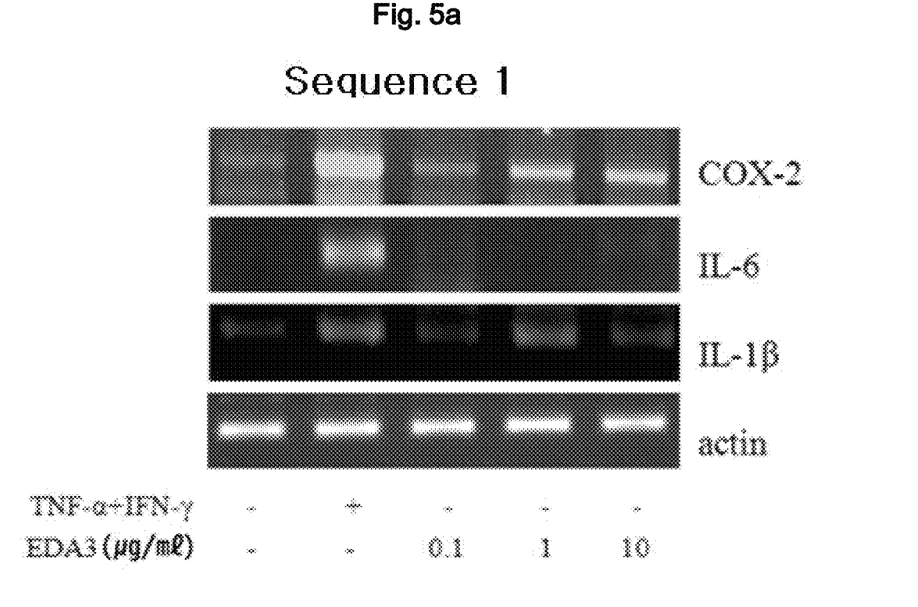
FIG. 5a is a RT-PCR analysis result showing that the expression of the down-stream proteins of COX-2, IL-6, IL-1b is remarkably enhanced after activation of NF-κB when treated with the peptide of SEQ ID NO:1 prepared in Preparation Example.
Figure 5B:
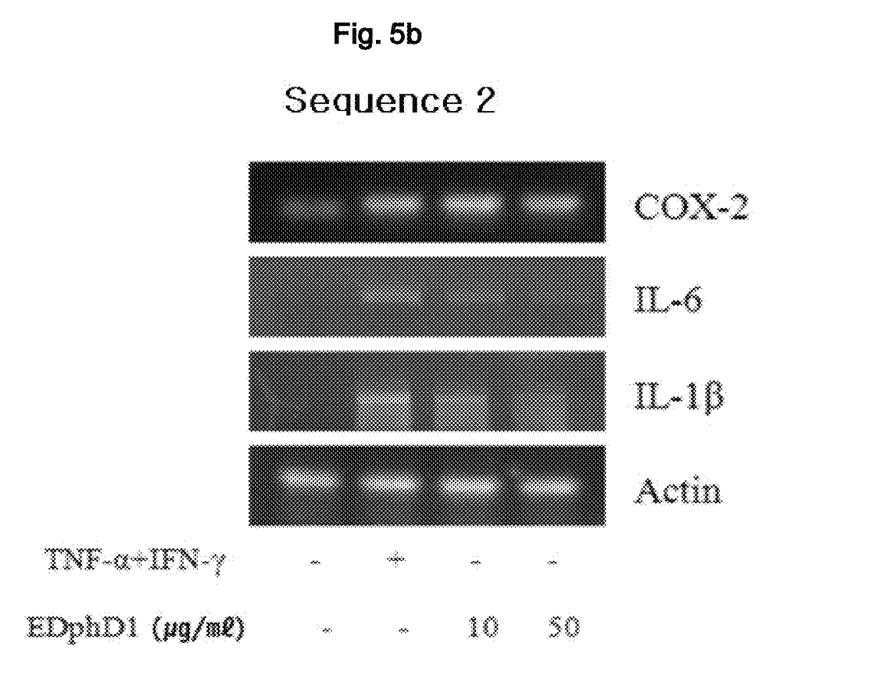
FIG. 5b is a RT-PCR analysis result showing that the expression of the down-stream proteins of COX-2, IL-6, IL-1b is remarkably enhanced after activation of NF-κB when treated with the peptide of SEQ ID NO:2 prepared in Preparation Example.

FIGS. 3a and 3b show the effect of IκB degradation through the phosphorylation followed by ubiquitination when treated with peptides of this invention. FIGS. 4a and 4b represent the effect of promoting the translocation of NF-κB into nucleus when treated with peptides of this invention. In addition, FIGS. 5a and 5b display that the expression of the down-stream proteins of COX-2, IL-6, IL-1b is remarkably enhanced after activation of NF-κB when treated with peptides of this invention.

Taken together in results of experimental Examples 1 and 2, it could be appreciated that the peptides of the present invention exerts excellent effects on promotion of hair growth through the activation of EDA1-EDAR signal.

Experimental Example 3

Influence of Peptides on Elevated Expression of Hair Follicle Stimulating Shh Protein To verify whether the peptides synthesized in preparation Example 1 enhances the expression of Shh protein which is known as EDA1 target molecule and to stimulate the hair follicle, kerationcytes ($3 \times 10^5$ cells) was added to each well of 96-well plates and cultured under 5% $CO_2$ for 24 hr at 37° C. After 24-hr culture, the medium was changed with a fresh medium without serum and cells were treated with empty sample (for normalization) and peptides synthesized aseptically dissolved in distilled water with the concentration of 10 μg/ml and cultured for 24 hr under the same conditions as described above. After that, the cell culture was collected and the expression level of Shh was measured through Western blotting using the specific antibody to Shh protein.

Figure 6A:
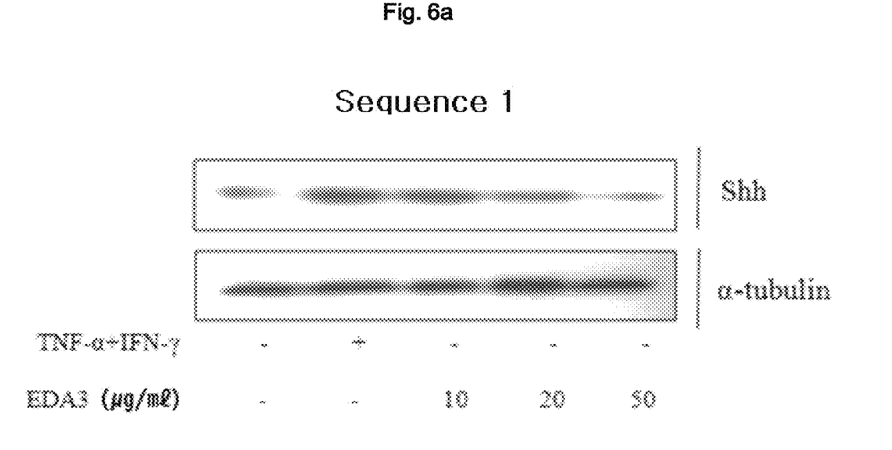
FIG. 6a is a Western blot analysis result representing that the expression of Shh protein, which is involved in the formation of hair follicle, is remarkably enhanced by the treatment with the peptide of SEQ ID NO:1 prepared in Preparation Example.
Figure 6B:
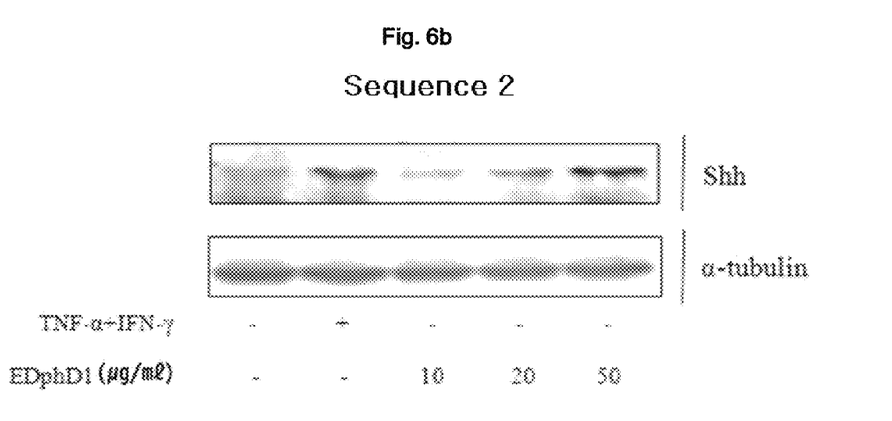
FIG. 6b is a Western blot analysis result representing that the expression of Shh protein, which is involved in formation of hair follicles, is remarkably enhanced by the treatment with the peptide of SEQ ID NO:2 prepared in Preparation Example.

As demonstrated in FIG. 6a, the expression level of hair follicle stimulating protein Shh is remarkably enhanced by the treatment of peptides in a concentration dependent manner. In addition, FIG. 6b shows that the expression level of Shh protein is remarkably enhanced by the treatment with the peptides in kerationcytes in concentration dependent manner.

Taken together, these results demonstrate that the peptides of the present invention exert hair production stimulating effect by inducing the hair follicle formation as well as by promoting hair growth through the EDA1-EDAR signal transduction.

Experimental Example 4

Analysis of Effects of Peptides on Mouse Hair Growth

The effect of cell proliferation was observed by treating mouse hair follicle cell derived from C57BL/6 mice with the peptide synthesized in Preparation Example 1. The cells harvested from hair follicle were added to each well of 96-well plates in a concentration of $3 \times 10^5$ cells and cultured under 5% $CO_2$ for 24 hr at 37° C. After 24-hr culture, the medium was changed with a fresh medium without serum and cells were incubated with empty sample (for normalization) and peptides synthesized aseptically dissolved in 10% distilled water with the respective concentrations of 10 μg/ml and 50 μg/ml for 72 hr under the same conditions as described above. After removing supernatants, cells were fixed with ethanol and then washed three times using PBS (phosphate buffered saline), followed by incubation with SRB solution. Cells were sufficiently washed with 1% acetic acid and observed under a microscope to find living cell condition. In addition, absorbance at 590 nm was measured to analyze cell viability (FIG. 7).

Figure 7:
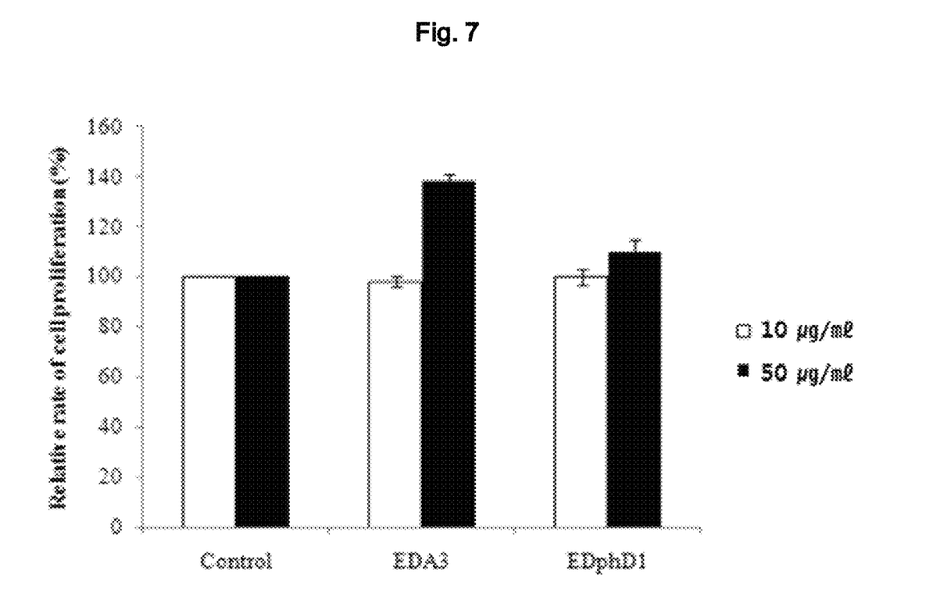
FIG. 7 is a graph representing the effect of promoting the cell growth in the mouse hair follicle by the treatment with the peptides prepared in Preparation Example.

FIG. 7 shows a graph representing the effect of promoting cell growth in mouse hair follicles by the treatment with the peptides. When treated with 50 μg/ml of the peptide, a relative significant increase of cell growth in mouse hair follicles was observed compared with control.

Example 1

Preparation of Nano Peptides 50 mg of two peptides synthesized in preparation Example were dissolved respectively in 500 ml of distilled water by sufficient agitation. The peptide solution was mixed with 5 g lecithin, 0.3 ml sodium oleate, 50 ml ethanol and a small amount of oils, and its volume was adjusted with distilled water to 1 L. The resulting solution was subjected to a microfluidizer under high pressure for emulsification, thereby providing nanosomes having about 100-nm size. The nanosomes were prepared to have a final concentration of about 50 ppm and used as ingredients for cosmetics.

Formulation Example 1

Skin Softener

A skin softener comprising peptide-containing nanosomes prepared in Example 1 was formulated according to the following composition:

TABLE 2

| Ingredients | Content (wt %) |
| --- | --- |
| Peptide nanosome | 2.5 |
| 1,3-butylene glycol | 6.0 |
| Glycerin | 4.0 |
| PEG 1500 | 1.0 |
| Sodium hyaluronate | 1.0 |
| Polysorbate 20 | 0.5 |
| Ethanol | 8.0 |
| Preservative, pigment | Proper amount |
| Benzophenone-9 | 0.05 |
| Perfume | Minute amount |
| Distilled water | Residual amount |
| Total | 100 |

Formulation Example 2

Nutrient Cream

A nutrient cream comprising peptide-containing nanosomes prepared in Example 1 was formulated according to the following composition:

TABLE 3

| Ingredients | Content (wt %) |
| --- | --- |
| Peptide nanosome | 2.5 |
| Meadowfoam oil | 3.0 |
| Cetearylalcohol | 1.5 |
| Stearic acid | 1.5 |
| Glyceryl stearate | 1.5 |
| Liquid paraffin | 10.0 |
| Wax | 2.0 |
| Polysorbate 60 | 0.6 |
| Sorbitan sesquiolate | 2.5 |
| Squalane | 3.0 |
| 1,3-butylene glycol | 3.0 |
| Glycerin | 5.0 |
| Triethanol amine | 0.5 |
| Tocopheryl acetate | 0.5 |
| Preservative, pigments | Proper amount |
| Perfume | Proper amount |
| Distilled water | Residual amount |
| Total | 100 |

Formulation Example 3

Nutrient Liquid

A nutrient liquid comprising peptide-containing nanosomes prepared in Example 1 was formulated according to the following composition:

TABLE 4

| Ingredients | Content (wt %) |
| --- | --- |
| Peptide nanosome | 2.5 |
| 1,3-butylene glycol | 4.0 |
| Glycerin | 4.0 |
| Cetearyl alcohol | 0.8 |
| Glyceryl stearate | 1.0 |
| Triethanol amine | 0.13 |
| Tocopheryl acetate | 0.3 |
| Liquid paraffin | 5.0 |
| Squalane | 3.0 |
| Makadamianut oil | 2.0 |
| Polysorbate 60 | 1.5 |
| Sorbitan sesquiolate | 0.5 |
| Carboxyvinyl polymer | 1.0 |
| Preservative, pigments | Proper amount |
| Perfume | Proper amount |
| Distilled water | Residual amount |
| Total | 100 |

Formulation Example 4

Essence

An essence comprising peptide-containing nanosomes prepared in Example 1 was formulated according to the following composition:

TABLE 5

| Ingredients | Content (wt %) |
| --- | --- |
| Peptide nanosome | 2.5 |
| Glycerin | 10.0 |
| 1,3-butylene glycol | 5.0 |
| PEG 1500 | 2.0 |
| Allantoin | 0.1 |
| DL-panthenol | 0.3 |

TABLE 5-continued

| Ingredients | Content (wt %) |
| --- | --- |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amount |
| Total | 100 |

Formulation Example 5

Hair Serum

A hair serum comprising peptide-containing nanosomes prepared in Example 1 was formulated according to the following composition:

TABLE 6

| Ingredients | Content (wt %) |
| --- | --- |
| Peptide nanosome | 1 |
| Glycerin | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amount |
| Total | 100 |

Formulation Example 6

Hair Toner

A hair toner comprising peptide-containing nanosomes prepared in Example 1 was formulated according to the following composition:

TABLE 7

| Ingredients | Content (wt %) |
| --- | --- |
| Peptide nanosome | 1 |
| Glycerin | 2.0 |
| 1,3-butylene glycol | 2.0 |
| PEG 1500 | 2.0 |
| Allantoin | 0.1 |
| DL-panthenol | 0.3 |
| EDTA-2Na | 0.02 |
| Sodium hyaluronate | 8.0 |
| Carboxyvinyl polymer | 0.2 |
| Triethanol amine | 0.18 |
| Octyldodeceth-16 | 0.4 |
| Ethanol | 10.0 |
| Perfume, preservative, pigments | Proper amount |
| Distilled water | Residual amount |
| Total | 100 |

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A peptide consisting of the amino acid sequence of SEQ ID NO:1.

2. A peptide consisting of the amino acid sequence of SEQ ID NO:1 and having at its N-terminal end a protection group selected from the group consisting of acetyl group, fluorenyl methoxy carbonyl group, formyl group, palmitoyl group, myristyl group, stearyl group and polyethylene glycol (PEG).

3. The peptide according to claim 1, wherein the peptide is derived from a human EDA (ectodysplasin A) protein.

4. The peptide according to claim 1, wherein the peptide facilitates cell proliferation in fibroblasts.

5. The peptide according to claim 1, wherein the peptide promotes EDA1-EDAR (EDA receptor) signal.

6. The peptide according to claim 1, wherein the peptide promotes the expression of Shh (Sonic hedgehog homolog) protein which induces the formation of hair follicles.

7. The peptide according to claim 1, wherein the peptide promotes cell growth in hair follicles.

* * * * *

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: EDA-derived peptide 1

<400> SEQUENCE: 1

Asn Met Ser Lys His Thr Thr Phe Phe Gly Ala
1               5                   10

<210> SEQ ID NO 2
<211> LENGTH: 12
<212> TYPE: PRT
<213> ORGANISM: Artificial Sequence
<220> FEATURE:
<223> OTHER INFORMATION: EDAR ligand-derived peptide 1

<400> SEQUENCE: 2

Leu Leu Ala Asp Thr Thr His His Arg Pro Trp Thr
1               5                   10
```